(12) United States Patent
Ahn et al.

(10) Patent No.: US 7,250,266 B2
(45) Date of Patent: Jul. 31, 2007

(54) SELECTIVE LABELING AGENT FOR PHOSPHOPROTEOME ANALYSIS AND PHOSPHORYLATED SITE ANALYSIS

(75) Inventors: Yeong Hee Ahn, Cheongju-shi (KR); Jong Shin Yoo, Daejeon-shi (KR); Jin Young Kim, Daejeon-shi (KR); Kun Cho, Daejeon-shi (KR)

(73) Assignee: Korea Basic Science Institute, Daejeon-shi (KR)

( * ) Notice: Subject to any disclaimer, the term of this patent is extended or adjusted under 35 U.S.C. 154(b) by 0 days.

(21) Appl. No.: 10/907,945

(22) Filed: Apr. 21, 2005

(65) Prior Publication Data

US 2005/0176093 A1    Aug. 11, 2005

(51) Int. Cl.
*G01N 33/00* (2006.01)
(52) U.S. Cl. .................................................... 435/7.92
(58) Field of Classification Search .................. None
See application file for complete search history.

(56) References Cited

U.S. PATENT DOCUMENTS

| | | | |
|---|---|---|---|
| 2002/0037532 A1 | 3/2002 | Regnier et al. | |
| 2002/0119505 A1* | 8/2002 | Goshe et al. | 435/7.92 |
| 2003/0017507 A1* | 1/2003 | Johnson | 435/7.5 |
| 2003/0054570 A1* | 3/2003 | Qiu et al. | 436/518 |
| 2003/0092076 A1 | 5/2003 | Regnier et al. | |
| 2004/0115821 A1 | 6/2004 | Robotti et al. | |

OTHER PUBLICATIONS

Conrads et al. New Tools for Quantitative Phosphoproteome Analysis; Biochemical and Biophysical Research Communications, vol. 290 (2002) pp. 885-890.*
Getz et al. A Comparison Between the Sulfhydryl Reductants Tris(2-Carboxyethyl)Phosphine and Dithiothreitol for Use in Protein Biochemistry; Analytical Biochemistry, vol. 273 (1999) pp. 73-80.*
Shapiro et al. Mechanism of Action of AET; Radiation Research, vol. 18 (1963) pp. 17-30.*
Thompson et al., "Characterization of Protein Phosphorylation by Mass Spectrometry~", Anal. Chem., Jul. 2003; 75 (13):3232-3243.
McLachlin and Chait, "Improved Beta-Elimination-Based Affinity Purification Strategy for Enrichment of Phosphopeptides", Anal. Chem., Dec. 2003; 75 (24):6826-6836.
Hale et al., "Increased Sensitivity of Tryptic Peptide Detection by MALDI-TOF Mass Spectrometry ~", Analytical Biochemistry, 2000; 287:110-117.
Steen and Mann, "A New Derivatization Strategy for the Analysis of Phosphopeptides by Precursor Ion ~", J Am. Soc. Mass Spectrom., 2002; 13:996-1003.
Rusnak et al., "Identification of Phosphorylated and Glycosylated Sites in Peptides by Chemically Targeted -", J of Biomolecular Techniques, Dec. 2002; 13 (4):228-237.
Oda et al., "Enrichment analysis of phosphorylated proteins as a tool for probing the phosphoproteome", Nature Biotechnology, Apr. 2001, 19:379-382.
Knight et al., "Phosphospecific proteolysis for mapping sites of protein phosphorylation", Nature Biotechnology, Sep. 2003, 21:1047-1054.

* cited by examiner

*Primary Examiner*—Jon Weber
*Assistant Examiner*—Paul Martin
(74) *Attorney, Agent, or Firm*—JHK Law; Joseph Hyosuk Kim

(57) ABSTRACT

Disclosed is a method of analyzing mass of the phosphoproteins or phosphopeptides and of analyzing phosphorylated positions at a phosphoprotein or phosphopeptide, comprising the steps of: 1) dephosphorylating at least one Ser and/or Thr residue of the phosphoprotein or phosphopeptide; 2) tagging the dephosphorylated amino acid residues with a tag having a R-L-G moiety wherein R is a nucleophilic functional group that selectively bind with dephosphorylated amino acid residues, G is selected from the group consisting of guanidine moiety or protected guanidine moiety such as a mono-N-protected guanidino group, a di-N,N'-protected guanidino group and an N'-protected guanidino group, and L is a linker linking the R and the G; and 3) subjecting the tagged proteins or peptides to mass spectrometry. The method is capable of precisely analyzing mass of phosphoproteins of trace amounts as well as positions of phosphorylated amino acids.

4 Claims, 3 Drawing Sheets

SELECTIVE LABELING AGENT FOR PHOSPHOPROTEOME ANALYSIS AND PHOSPHORYLATED SITE ANALYSIS

CROSS REFERENCE TO RELATED APPLICATIONS

This Application claims benefit to PCT/KR04/00256, filed Feb. 10, 2004, which is hereby incorporated by reference in its entirety.

TECHNICAL FIELD

The present invention relates to a method of analyzing mass of the phosphoprotein or phosphopeptide and of analyzing phosphorylated positions at a phosphoprotein or phosphopeptide. Also, the present invention is concerned with a selective labeling agent useful in the method.

BACKGROUND ART

Proteins play crucial roles in virtually every biological process. The analysis and identification of proteins at the molecular level is, therefore, very significant and necessary for understanding the versatile biological activities of cells and, further, for developing new therapies for diseases.

Most proteins undergo some form of modification following translation. Most representative of the post-translational modification is phosphorylation. Most commonly occurring on tyrosine, serine, threonine, histidine and lysine residues, phosphorylation plays critical roles in the regulation of many cellular processes.

Particularly, reversible phosphorylation is known to be closely related to intra- and inter-cellular signaling events. Many of the proteins involved in cell signaling pathways are phosphorylated by kinases and dephosphorylated by phosphotases. Many reported that abnormal phosphorylation/dephosphorylation of specific proteins is causative in many diseases.

Fast and accurate screening for the irregularity of proteins in phosphorylation state is very helpful for understanding intra- or inter-cellular signaling events as well as contributing to the development of effectively diagnosing methods for diseases.

Tandem mass (MS/MS) spectrometry, which is one of the most potent protein analysis methods in current use, requires the hydrolysis of proteins to smaller mass peptides for analysis. The tandem mass spectrometry suffers some disadvantages when analyzing phosphopeptides, unlike the case of non-phosphopeptides. First, protein phosphorylation is usually reversible so that the sites on which phosphorylation can occur may be partially phosphorylated. Thus, in many cases, the amount of phosphopeptides obtained after the hydrolysis of proteins is present substoichiometrically. Second, the phosphoric acid groups present in phosphopeptides give a significant ionization suppression effect in cation mass spectrometry, which is generally adopted in peptide analysis. As a result, the detection sensitivity of phosphopeptides is very poor in relation to that of non-phosphopeptides. Finally, as phosphoric acid groups are chemically unstable, phosphopeptides may be partially dephosphorylated during their mass analysis. If dephosphorylation occurs, not only reduce the detection sensitivity but also complicate the spectrum interpretation, resulting in an incomplete MS/MS sequencing analysis of peptide.

To avoid these problems, β-elimination of phosphoric acid groups is used. When being subjected to β-elimination in a basic solvent, phosphoserine and phosphothreonine residues of peptides or proteins are converted into dehydroalanine and β-methyldehydroalanine residues, respectively. In advance of mass spectrometry, phosphoric acid groups are removed from sample peptides or proteins. The elimination of phosphoric acid groups from peptides or proteins is accompanied by the removal of the above-mentioned problems, such as the ionization suppression due to the presence of phosphoric acid groups, and the partial dephosphorylation attributed to the chemical instability of phosphoric acid groups. However, the residues resulting from the dephosphorylation, that is, dehydroalanine and β-methyldehydroalanine are unstable, as well. In order to make the dephosphorylated peptide stable, the residues are rendered to undergo Michael addition reactions with properly-designed, various nucleophiles. Consequently, the problems of phosphopeptides on mass spectrometry can be solved through dephosphorylation, and the analysis of phosphopeptides is facilitated by introducing tag with versatile information such as specific mass number into the dephosphorylated amino acid residues.

Tags, used in β-elmination/Michael addition reaction, generally contain sulfhydryl functionality. The tags can also have neutral functional groups or basic functional groups such as amine groups promoting the generation of cations in peptides. Thus the mass sensitivity of the tagged peptides is exceptionally improved. The tagged peptide derivatives are also so stable under general mass spectrometric conditions that accurate amino acid sequencing can be achieved using MS/MS spectrometry.

Another advantage of phosphospecific tagging method is that relative quantification between samples obtained from different sources can be achieved by using stable isotope-coded tag. When compared to intact tag, stable isotope-coded tag shows the same reactivity in the β-elimination/addition reaction and no different analysis sensitivity in mass spectrometry. Only difference between intact tag and stable isotope-coded tag in mass spectrometry is mass values read on mass spectra of each peptide derivatives. Thus the intact tag and the stable isotope-coded tag are used together but separately for tagging of each sample so that relative quantification can be achieved between samples obtained from different sources.

A further advantage provided by the β-elimination/addition reaction is that only tag derivatives of phosphopeptides can be selectively purified and concentrated by introducing an appropriate functional group having affinitive interactivity to tag. For example, a tag having biotin structure is used the purpose (Oda, Y. et al., 2001, Nature Biotechnology, 19, 379-382). When a biotin group is linked through ethanedithiol to a dephosphorylated residue, streptavidin which can affinitively interact with biotin can be used to selectively isolate and concentrate the tagged peptides formerly phosphopeptides from sample. Various neucleophiles containing a thiol group are used to label phosphopeptides and proteins.

None the less, there is a need of an improved mass spectrometry method for effectively analyzing phosphoproteins which are present in the body in trace amounts or in substoichiometric amounts due to partial phosphorylation as well as the phosphorylated sites of the proteins.

DISCLOSURE OF THE INVENTION

It is an object of the present invention to provide a selective labeling agent for phosphorylated amino acid residues, with which trace amounts of phosphoproteins can be analyzed at high detection sensitivity by mass spectrometry.

It is another object of the present invention to provide a method of analyzing mass of the phosphoprotein or phosphopeptide and of identifying phosphorylated positions at a phosphoprotein or phosphopeptide, with the aid of the selective labeling agent.

It is a further object of the present invention to provide a method of relatively quantifying a phosphoprotein or phosphopeptide between samples obtained from different sources.

In accordance with an aspect of the present invention, there is provided a method of analyzing mass of the phosphoprotein or phosphopeptide and of analyzing phosphorylated positions at a phosphoprotein or phosphopeptide, comprising the steps of:

1) dephosphorylating at least one Serine and/or Threonine residue of the phosphoprotein or phosphopeptide;
2) tagging the dephosphorylated amino acid residues with a tag having a R-L-G moiety wherein R is a nucleophilic functional group that selectively bind with dephosphorylated amino acid residues, G is selected from the group consisting of guanidine moiety or protected guanidine moiety such as a mono-N-protected guanidino group, a di-N-protected guanidino group and an N'-protected guanidino group, and L is a linker linking the R and the G; and
3) subjecting the tagged protein or peptide to mass spectrometry.

In accordance with another aspect of the present invention, there is provided a peptide-reactive tag, suitable for use in the method.

In accordance with a further aspect of the present invention, there is provided a method of relatively quantifying a phosphoprotein or phosphopeptide between samples obtained from different sources and of identifying phosphorylation positions in the phosphoprotein or phosphopeptide, comprising the steps of: 1) tagging two peptide samples with the intact tag and the stable isotope-coded tag, respectively; and 2) admixing the two peptide samples and subjecting the admixture to mass spectrometry.

BEST MODES FOR CARRYING OUT THE INVENTION

The present invention provides a method of analyzing mass of the phosphoprotein or phosphopeptide and of analyzing phosphorylated positions at a phosphoprotein or phosphopeptide, comprising the steps of:

1) dephosphorylating at least one Serine and/or Threonine residue of the phosphoprotein or phosphopeptide;
2) tagging the dephosphorylated amino acid residues with a tag having a R-L-G moiety wherein R is a nucleophilic functional group that selectively bind with dephosphorylated amino acid residues, G is selected from the group consisting of guanidine moiety or protected guanidine moiety such as a mono-N-protected guanidino group, a di-N,N'-protected guanidino group and an N'-protected guanidino group, and L is a linker linking the R and the G; and
3) subjecting the tagged protein or peptide to mass spectrometry.

In the first step, to analyze the mass of the phosphoprotein or phosphopeptide and phosphorylated positions at a phosphoprotein or phosphopeptide, dephosphorylation is conducted on at least one serine and/or threonine residue of the phosphoprotein or phosphopeptide in the present invention.

It is preferred that a variety of the phosphoproteins or phosphopeptides to be analyzed are prepared according to the lapse of expression time, environments or nutritive states, and diseases or their severity from different organ tissues and different intracellular sub-organelles. For the convenience of protein purification, the protein material may be pre-treated through, for example, denaturation, reduction, cysteine alkylation and/or deglycosylation. Additionally, the protein material may be partially isolated or purified by well-known techniques such as 2D PAGE, affinity chromatography, etc.

After appropriate pre-treatment, phosphoproteins of high molecular weights are preferably digested to peptide fragments of low molecular weights by use of a proteinase. For example, trypsin is used to cleave the amide bond at lysine site and arginine site.

Figure 1:
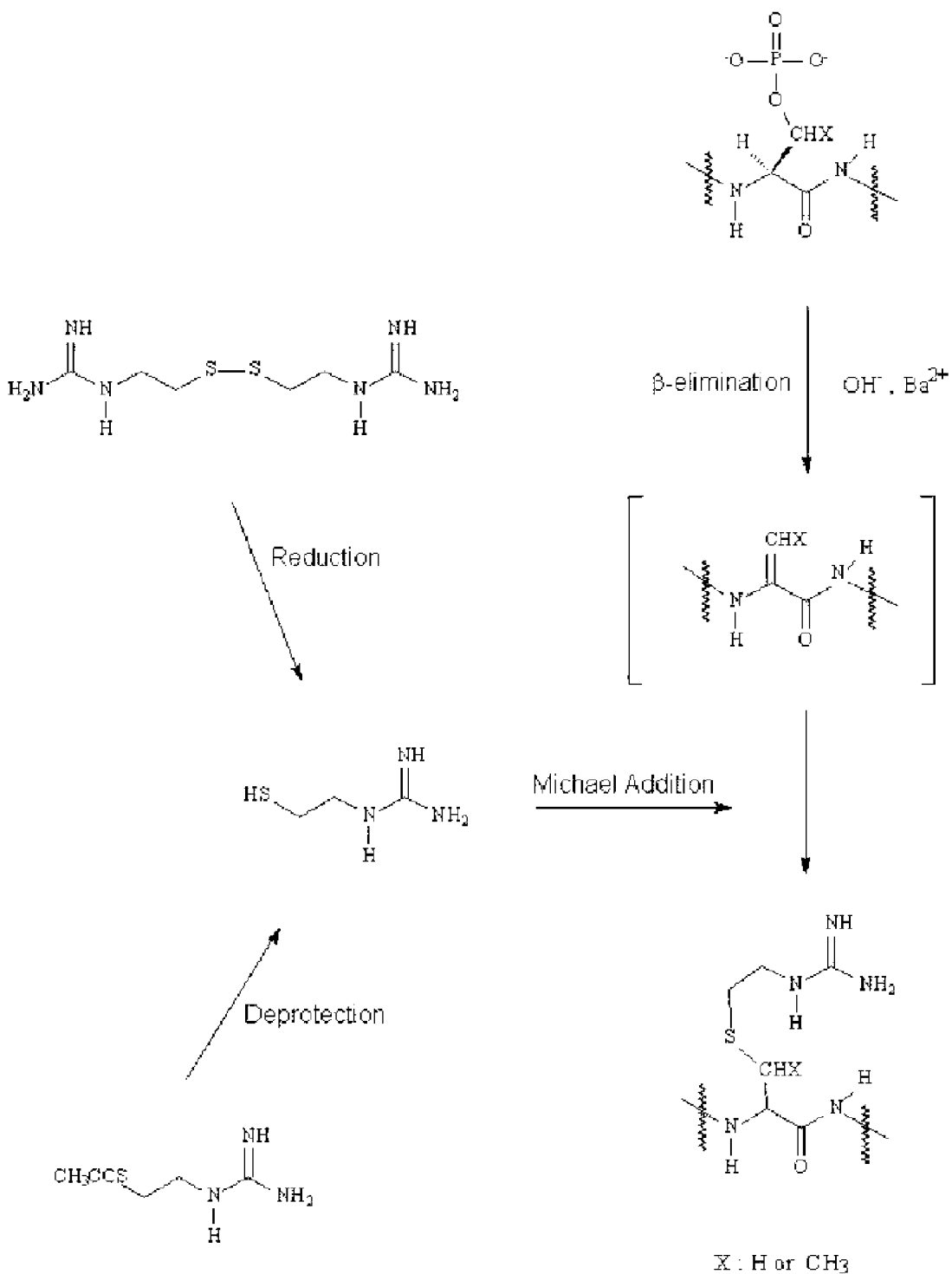
FIG. 1 is a reaction scheme showing a tagging process in which a phosphopeptide is dephosphorylated at a phosphoserine residue (X=H) or a phosphothreonine residue (X=CH$_3$) through β-elimination, and tagged through a Michael addition reaction.

In the invention, it is preferred to perform the dephosphorylation through the β-elimination represented by the following reaction formula 1 (see FIG. 1)

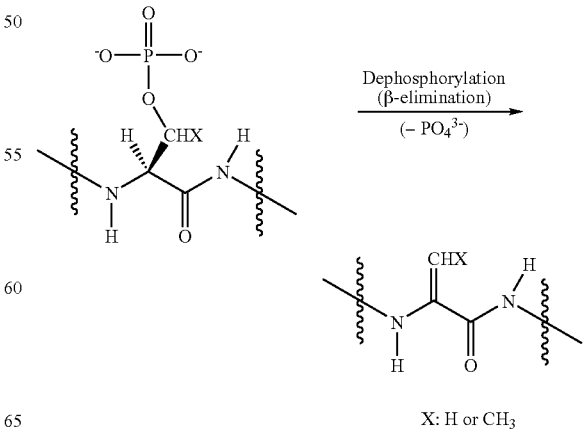

X: H or CH$_3$

In the reaction formula 1, the amino acid residue is serine for X=H and threonine for X=CH$_3$.

The dephosphorylation of phosphorylated amino acid residues through β-elimination is preferably performed in alkaline aqueous solutions or alkaline aqueous solution containing water-soluble organic solvents. Able to cause the dephosphorylation, various bases can be used in the alkaline solutions. Preferred bases are alkoxides such as hydroxide, methoxide and ethoxide. In addition, in order to prevent undesired peptide degradation and promote the β-elimination in the alkaline condition, the reaction is preferably conducted in the presence of a metal cation which can catalyze the β-elimination. Suitable as the catalyst are the metal cation selected from Group II elements in the periodic table. Preferably, the catalyst is selected from the group consisting of Mg$^{2+}$, Ca$^{2+}$, Sr$^{2+}$, and Ba$^{2+}$.

In the presence of the metal cation as a catalyst, the β-elimination can be effectively accomplished in a reasonably mild alkaline condition without raising the temperature of the reaction and using a non-volatile polar organic solvent such as dimethylformamide (DMF) and dimethylsulfoxide (DMSO). If a non-volatile polar organic solvent is used, there may be vexatious problems in the chromatographic purification or mass analysis process which may follow the tagging reaction. In a preferred embodiment for the β-elimination according to the present invention, a NaOH solution containing BaCl$_2$ is used as an alkaline solution and a metal catalyst source.

After the removal of phosphate group through the β-elimination, phosphorylated serine is converted to dehydroalanine, and phosphorylated threonine to β-methyldehydroalanine. The site from which the phosphate group is removed can act as a good receptor for neucleophilic tags containing thiol functionality. Afterwards, the protein or peptide is labeled with the tags through the Michael addition.

In the second step, the dephosphorylated amino acid residues are labeled with a peptide-reactive tag having a R-L-G moiety through the addition reaction represented by the following reaction formula 2 (see FIG. 1):

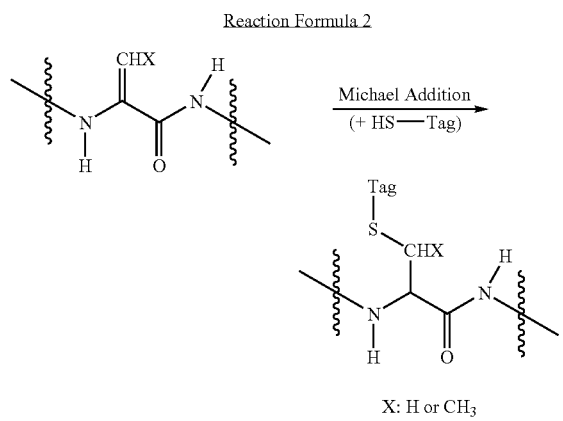

X: H or CH$_3$ wherein the amino acid residue is dehydroalanine for X=H and β-methyldehydroalanine for X=CH$_3$.

The peptide-reactive tag, represented by R-L-G, consists of a nucleophilic functional group (R) selectively binding with dephosphorylated amino acid residues, a basic functional group (G) having proton affinity, and a linker (L) connecting the nucleophilic functional group to the basic functional group.

Serving as a nucleophile, the functional group R causes an addition reaction at the α,β-conjugate system formed by the dephosphorylation of phosphorylated amino acids through β-elimination. Among a variety of functional groups having nucleophilicity, nucleophile having sulfhydryl group is preferable.

In order to increase the detection sensitivity of the tagged peptides, the basic functional group G of the tag may be preferably a guanidine group having high affinity for proton.

Generally, a basic amino group (—NH$_2$), serving as an electron-pair donor, facilitates cation formation and thus tends to increase the detection sensitivity of peptides in mass analysis processes. Recently, phosphopeptides have been analyzed by use of aminoethanethiol as a chemical tag (Thompson, A. J. et al., 2003, *Analtytical Chemistry*, 75, 3232-3243). In addition, the detection sensitivity of peptides was greatly increased by converting the amino group present on the side chain of the C-terminal lysine to a guanidino group (Hale, J. E. et al., 2000, *Analytical Biochemistry*, 287, 110-117). In the present invention, however, a tag having a guanidiono group inherently is used to label phosphorylated amino acid residues of a phosphopeptide, so that the peptides labeled with the tag show high cationization tendency and great detection sensitivity. The guanidino group include mono-N-protected guanidino groups, di-N,N'-protected guanidino groups, N'-protected guanidino group and non-protected guanidino, preferably include non-protected guanidine.

When containing a sulfhydryl group, the tag may be represented by the following structural formula: HS-Linker-NHCNH(NH$_2$). Sulfhydryl group can also be generated from its precursor form, disulfide or thioester etc. In the case of containing a disulfide group of sulfhydryl, the tag may be represented by the following structural formula: (H$_2$N) HNCHN-Linker-S-S-Linker-NHCNH(NH$_2$).

When thiol groups are in the form of disulfide, it is of no nucleophilicity: disulfide must be reduced to sulfhydryl which is so nucleophilic as to cause a Michael addition. To this end, the disulfide of no nucleophilicity is reduced just before or at the same time as the tagging reaction of the phosphopeptide, so that the reduced form can act as a nucleophile without an additional purifiation process. As the tag is reduced from its disufide form and directly used for tagging without purification, the reducing agent used must not have a negative influence on the addition reaction. Thus, thiol lineage reducing agents (e.g., ethanedithiol, mercaptoethaneol, dithiothreitol, etc.) are not suitable because they can act as a nucleophile-like tag. Organophosphine, especially, trialkylphosphines are suitable as reducing agents meeting the conditions and preferably selected from the group consisting of tris(2-cyanoethyl)phosphine (TCNEP), tris(2-carboxyethyl)phosphine (TCEP), tris(hydroxypropyl) phosphine (THPP) and tributylphosphine (TBP). Additionally, the reducing agent is preferably in an immobilized form. The reducing agent not only reduces the tag but also functions to prevent the oxidation of the tagged peptide or protein in subsequent analysis processes.

Alternative precursors for the sulfhydryl group include thioester, dithioester and thioether. Particularly, thioester (e.g., thioacetate) is preferable because the protecting group can be beforehand deprotected in the alkaline condition which is used for the addition reaction.

In another embodiment, not only the thiol group but also the guanidine group (G) showing a high proton affinity can be protected by an appropriate protecting group. The guanidino moiety (G) is selected from the group consisting of a mono-N-protected guanidino group, a di-N,N'-protected guanidino group, N'-protected guanidino group, and a non protected guanidino group. Preferably, the guanidino-protected tag may be represented by the following structural formula: $PG_1$-S-Linker-NHCNH(NH)-$PG_2$. ($PG_1$: H or thiol protecting group). In the above structural formula, $PG_2$, serving to protect the guanidino group, can be deprotected before the addition reaction when being unstable in alkaline conditions and or after the addition reaction when being stable in basic conditions.

Linking the strong nucleophile thiol group and the strong protophile guanidino group, the linker has an appropriate size and structure. Although adopting various structures depending on isolation and analysis techniques for tagged peptides, the backbone of the linker is generally based on hydrocarbon, ethylene oxide or peptide. The tag is also prepared from its precursor form or protected form. The linker connecting the protophilic guanidine with nucleophilic sufhydryl group provides a space where a stable isotope is substituted for the purpose of quantifying relatively phosphopeptides. For example, a tag having an isotopically substituted linker can exhibit a mass difference on mass spectra without chemical difference, thereby facilitating the relative quantification of phosphopeptides obtained from different sources. The stable isotope useful in the present invention is selected from the group consisting of $^2H$, $^{13}C$, $^{15}N$, $^{17}O$, $^{18}O$ and $^{34}S$. High sensitivity mass analysis of phosphospecific tagged peptides requires that the linker should not be excessively large in size (mass), show few negative factors such as steric factor in the addition reaction, and be chemically stable under reaction conditions for the addition reaction and mass analysis conditions.

As one of a preferable phosphospecific tag in the present invention, guanidinoalkanethiol or guanidinoethanethiol is selected. Guanidinoethanethiol (GET) is more preferable as a tag. Guanidinoethanethiol (GET) can also be prepared from reduction of its precursor, guanidinoethanedisulfide (GEDS), beforehand by an appropriate reducing agent. Like general thiol reagents, the thiol group of GET is readily oxidized to GEDS when being exposed to air.

The mass analysis for tagged sample is conducted preferably after chromatographic purification of the reagents. Since the reagents for the tagging, including the tag, are inorganic or water-soluble with high polarity, they can be removed from the peptides by use of various analysis techniques based on reverse phase chromatography or affinity chromatography.

Not only the tag prepared in the present invention but also the method of analyzing phosphorylation positions at phosphoproteins by use of the tag can be effectively used to understand the phosphorylation states in various proteins. Because unstable phosphate group is removed and relatively stable tags, which are able to increase the mass sensitivity of tagged peptides, are introduced instead of phosphate group, the mass analysis sensitivity of the peptides is greatly increased and MS/MS sequencing can be facilitated. The characteristic mass change of phosphopeptides due to the introduction of the tag in phosphopeptides allows the phosphopeptide to be easily discriminated from non-phosphorylated peptides in the third step.

Enzymatic hydrolysis of a phosphoprotein produces a mixture in which phosphopeptides and peptides having no phosphorylated amino acid residues coexist. The mixture may be subjected to the tagging reaction. However, in order to obtain well-understandable analysis data, non-phosphorylated peptides are removed from the phosphopeptides by use of various methods such as immobilized metal affinity chromatography (IMAC) before the tagging process can be applied to the digested peptides. IMAC being used for enrichment of phosphopeptides from peptide mixture can be utilized in combination with the tagging method in advance of the tagging reaction. Alternatively, the tagged protein of said step 3 can be also hydrolyzed to tagged peptide by proteolytic enzyme before the mass spectrometry.

If a functional group showing specific affinity has been introduced to a chemical tag beforehand, the peptides tagged with the tag can be selectively isolated and enriched. A fluorescent tag in which a fluorescent dye has been introduced to a tag allows the tagged peptides to be detected and analyzed with high sensitivity.

The present invention also provides a method for relative quantification of phosphorylation degrees between phosphopeptides present in samples obtained from different sources. For relative quantification, a sample is tagged with a tag while the other, obtained from different sources or states, is separately tagged with a stable, isotopically labeled tag. The two tags are the same chemically, but different in mass. After the two test materials are combined, mass analysis gives pair peaks which show a predetermined mass difference on mass spectrometry. From the relative intensities of the peaks, the phosphopeptide present in each of the samples can be relatively quantified.

Therefore, the protein phosphorylation difference between organ tissues and between intracellular tissue sites according to the lapse of expression time, according to environments or nutritive states, and according to diseases or disease severity can be relatively quantified by the tagging method. Additionally, the analysis method of the present invention can be applied for studies of identifying materials which have influence on protein phosphorylation, and thus, for the diagnosis of diseases and the development of therapies.

A better understanding of the present invention may be obtained by reading the following examples which are set forth to illustrate, but are not to be construed to limit the present invention.

EXAMPLE 1

Sample Preparation

For the convenience purification, a standard protein or a protein exacts to be analyzed was pre-treated according to well-known methods. A protein sample was denatured in 6M guanidine hydrochloride and then, allowed to contact with TCEP (Tris(2-carboxyethyl)phosphine) HCl for 1 hour at 37° C. to reduce the disulfide bonds of cystein residues. Reduced cystein residues were protected by use of an alkylating reagent such as iodoacetamide or oxidized by use of performic acid. Excessively used reagents were removed through gel filtration or dialysis. O-Linked oligosaccharide which might be present in proteins were removed by use of O-glycanase in advance of a tagging process lest it caused the β-elimination, like phosphate groups, under an alkaline tagging condition. However, although β-casein represented by SEQ ID NO:1, used as a standard protein in the present invention, has O-linked oligosaccharide, its β-elimination was not observed under an optimized tagging condition. After protein digestion with protease such as trypsin, the tagging reaction was carried out using hydroxide ions as a base in the presence of barium cations as a catalyst. Alternatively, phosphopeptides were enriched through immobilized metal affinity chromatography (IMAC) prior to the tagging process.

EXAMPLE 2

Tagging of Phosphopeptides

A tagging reagent solution was prepared by dissolving 20 μmol of guanidinoethanethiol (GET) in 30 μl of distilled water. When a disulfide precursor of GET was used as a tagging reagent, 10 μmol of guanidinoethanedisulfide 2 hydrochloride (GEDS 2HCl) was dissolved in 10 μl of distilled water, added with 20 μl of tris(2-cyanoethyl)phosphine (TCNEP) (500 mM), and let to stand for about 30 min at 45° C. to produce a tagging reagent solution. A peptide sample (about 20 μg) obtained by drying the pretreated protein sample of Example 1 in a vacuum condition was dissolved in 13 μl of distilled water and then mixed with 43 μl of the tagging reagent solution prepared above. The mixture solution were sequentially added with 6 μl of 5.0 N NaOH and 2 μl of 1.0 M $BaCl_2$ and reacted for about 2-3 hours at 45° C. After being cooled to 5° C. or less, the reaction solution was neutralized with 1.0% aqueous acetic acid solution. Prior to analysis, the reaction solution was diluted with 0.1% acetic acid or trifluoroacetic acid solution.

EXAMPLE 3

Analysis of GET-Tagged Peptide

Liquid chromatography/the matrix-assisted laser desorption ionization mass spectrometry (LC/MALDI MS) and liquid chromatography/the electrospray ionization mass spectrometry (LC/ESI MS) are very useful for the analysis of tagged peptides. The tagged peptide samples could be purified easily through reverse phase chromatography because all of the reagents used in the tagging process were highly hydrophilic organic materials of low molecular weight, or inorganic salts. Subsequently, peptides separated by gradient elution were subjected to mass analysis by being introduced directly into an ESI mass spectrometer, or loaded on MALDI sample plates and analyzed by MALDI TOF mass spectrometer. Peptide sequencing was conducted by MALDI TOF/TOF (time-of-flight/time-of-flight) mass spectrometer.

Figure 2A:
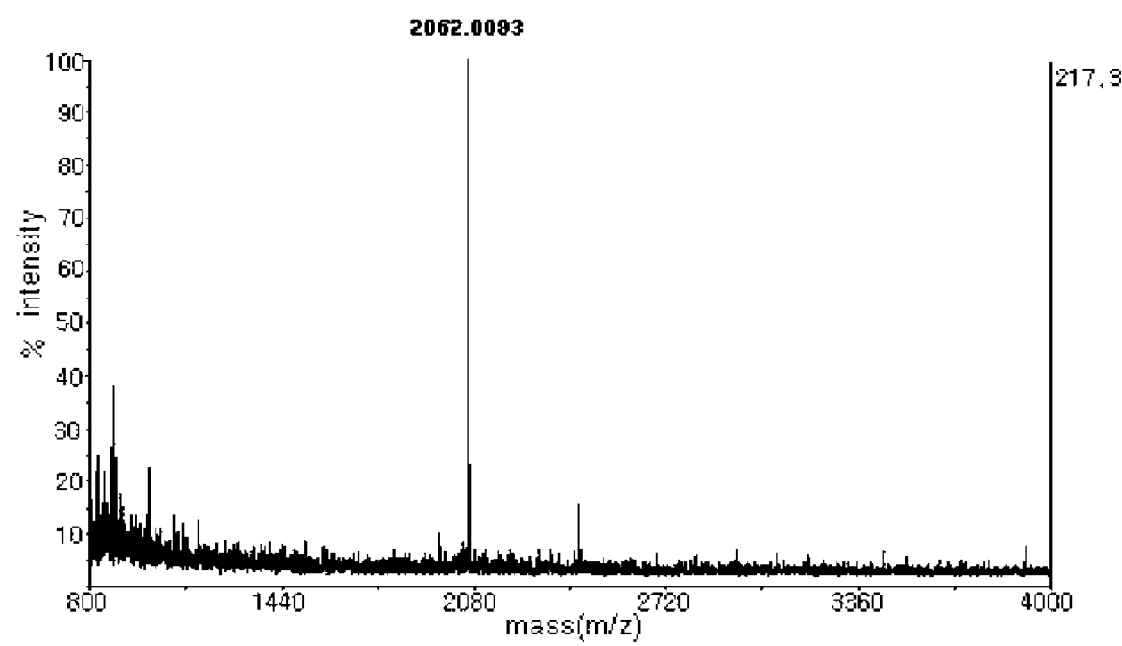
FIG. 2a is a mass spectrum of a β-casein monophosphopeptide (10 pmol) represented by SEQ ID NO:1 wherein the third amino acid residue serine is phosphorylated.

The phosphopeptide obtained by the trypsin digestion of the phosphoprotein β-casein represented by SEQ ID NO:1 (FQS$^P$EEQQQTEDELQDK where S$^P$ stands for phosphorylated serine), was analyzed at a mass number which was higher by m/z 21 when being tagged with GET-TAG (FIG. 2b, M/Z 2083.002 peak) than when being not tagged with the tag (FIG. 2a, m/z 2062.0083 peak). Therefore, specific changes in the mass number of peptides are very useful in discriminating phosphopeptides from non-phosphorylated peptides.

Figure 2B:
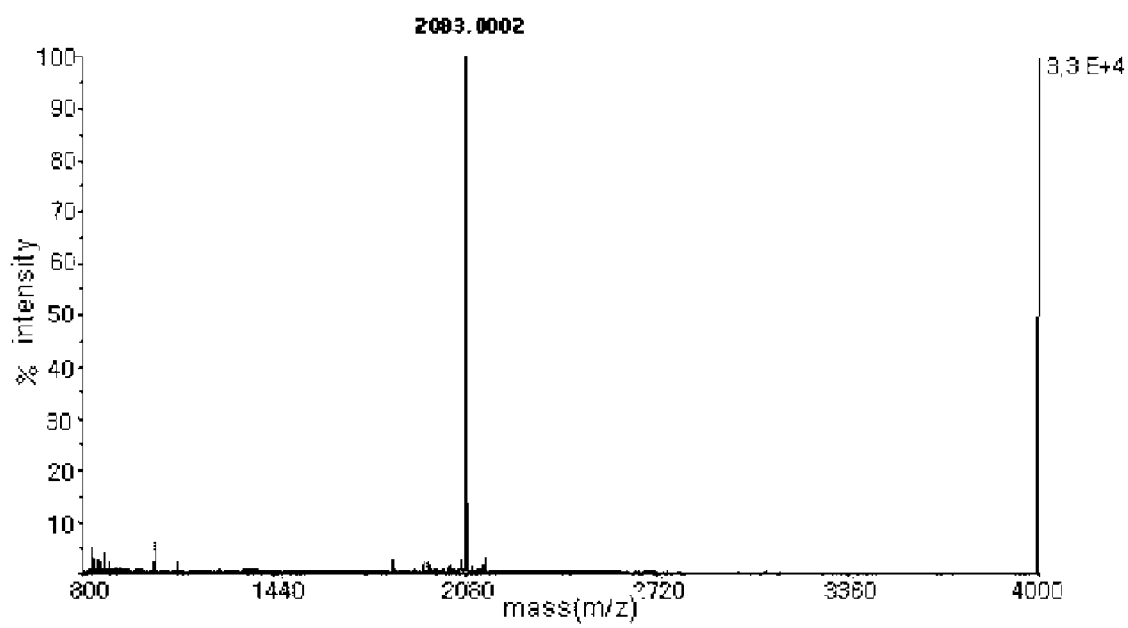
FIG. 2b is a mass spectrum of the GET-tagged peptide (10 pmol) derived from β-casein monophosphopeptide represented by SEQ ID NO:1, wherein phosphoserine, the third amino acid residue, has been converted to guanidinoethylcysteine (GEC) with increased mass (m/z+21).

The phosphopeptide sample was analyzed in an amount of about 10 pmol without being tagged (FIG. 2a) and in an amount of about 1 pmol after being tagged (FIG. 2b). The peak intensity of the tagged sample, even though it was used in a lower amount, is greater than that of the non-tagged sample. Consequently, the analysis of the present invention greatly improves the detection sensitivity for phosphopeptides.

Figure 3:
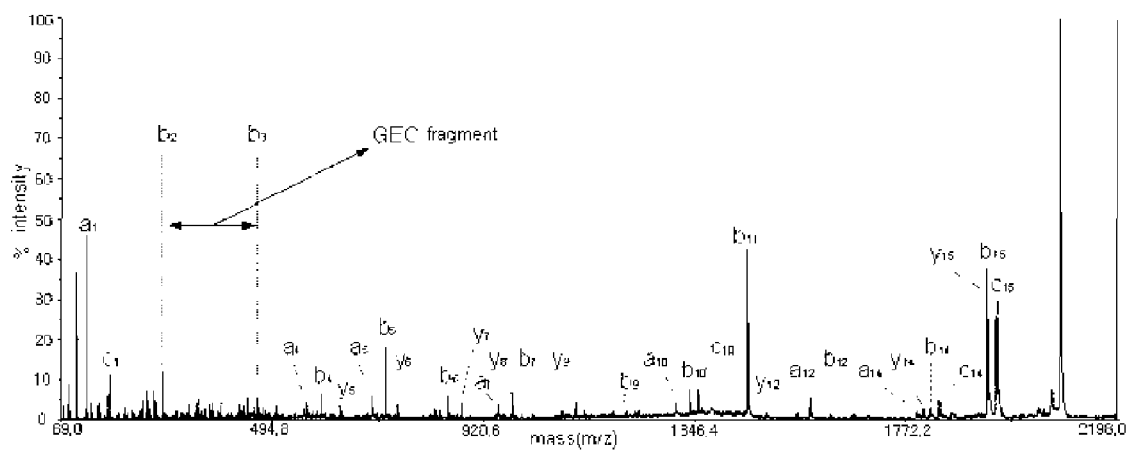
FIG. 3 is an MS/MS spectrum of the GET-tagged peptide derived from β-casein monophosphopeptide represented by SEQ ID NO:1. Peaks corresponding guanidinoethylcysteine (GEC) fragment denote the third amino acid residue of the peptide had been phosphorylated before.
Figure 4:
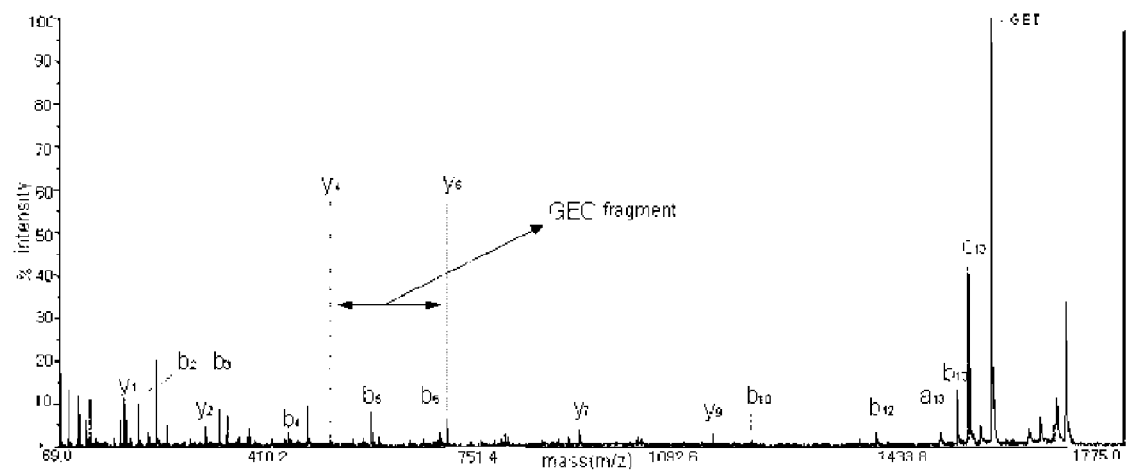
FIG. 4 is an MS/MS spectrum of the GET-tagged peptide derived from α-casein monophosphopeptide represented by SEQ ID NO:2. Peaks corresponding guanidinoethylcysteine (GEC) fragment denote the tenth amino acid residue of the peptide had been phosphorylated before.

As phosphorylated serine was converted to guanidinoethylcysteine (GEC) by the tagging process, there were read $b_2$ and $b_3$ peaks in MS/MS spectrum of the tagged peptide, whose gap is the same as the mass difference of m/z 188.0 corresponding to a GEC fragment ion (FIG. 3). Hence, phosphorylation positions inside peptides can be easily determined by MS/MS analysis.

In the MS/MS analysis of the GET-tagged peptide of α-casein represented by SEQ ID NO:2 (VPQLEIVP-NS$^P$AEER), there were shown y4 and y5 peaks between which the gap is identical to the mass difference of m/z 188.0 corresponding to a fragment ion of GEC.

Taken together, the data obtained above demonstrates that the novel tag and tagging method developed in the present invention is very useful to analyze phosphopeptides with high sensitivity and to determine phosphorylation positions in peptides.

INDUSTRIAL APPLICABILITY

The method is capable of precisely analyzing mass of phosphoproteins of trace amounts as well as positions of phosphoryated amino acids. Therefore, the method can be used for studies of biological functions of various proteins according to their phosphorylation states, and for diagnosing various diseases.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A method of analyzing mass of phosphoproteins or phosphopeptides and of analyzing phosphorylated positions at a phosphoprotein or phosphopeptide, comprising the steps of:
   a) dephosphorylating at least one Serine and/or Threonine residue of the phosphoproteins or phosphopeptides;
   b) tagging the dephosphorylated amino acid residue with guanidinoethanethiol to produce tagged proteins or peptides; and
   c) subjecting the tagged proteins or peptides to mass spectrometry.

2. The method as set forth in claim 1, wherein the phosphopeptides of the step a) are prepared by hydrolyzing phosphoproteins chemically or enzymatically, said phosphoproteins being obtained from various organ tissues, intracellular organelles or membrane proteins.

3. The method as set forth in claim 1, wherein the tagged proteins of step c) are hydrolyzed to tagged peptides enzymatically or chemically, before the mass spectrometry.

4. A method of relatively quantifying a phosphoprotein or phosphopeptide between samples obtained from different sources and of identifying phosphorylation positions in the phosphoprotein or phosphopeptide, comprising the steps of:
   tagging two peptide samples with the isotopically unlabeled guanidinoethanethiol and with isotopically labeled guanidinoethanethiol wherein the isotopes are selected from the group consisting of $^{2}H$, $^{13}C$, $^{15}N$, $^{17}O$, $^{18}O$, and $^{34}S$, respectively; and
   admixing the two peptide samples and subjecting the admixture to mass spectrometry.

* * * * *

SEQUENCE LISTING

```
<160> NUMBER OF SEQ ID NOS: 2

<210> SEQ ID NO 1
<211> LENGTH: 16
<212> TYPE: PRT
<213> ORGANISM: Unknown
<220> FEATURE:
<223> OTHER INFORMATION: fragment of beta-casein
<220> FEATURE:
<221> NAME/KEY: MOD_RES
<222> LOCATION: (3)
<223> OTHER INFORMATION: PHOSPHORYLATION,

<400> SEQUENCE: 1
```

```
Phe Gln Ser Glu Glu Gln Gln Thr Glu Asp Glu Leu Gln Asp Lys
 1               5                  10                  15

<210> SEQ ID NO 2
<211> LENGTH: 14
<212> TYPE: PRT
<213> ORGANISM: Unknown
<220> FEATURE:
<223> OTHER INFORMATION: fragment of alpha-casein
<220> FEATURE:
<221> NAME/KEY: MOD_RES
<222> LOCATION: (10)
<223> OTHER INFORMATION: PHOSPHORYLATION,

<400> SEQUENCE: 2

Val Pro Gln Leu Glu Ile Val Pro Asn Ser Ala Glu Glu Arg
 1               5                  10
```